US006451532B1

United States Patent
McKiernan et al.

(10) Patent No.: US 6,451,532 B1
(45) Date of Patent: *Sep. 17, 2002

(54) ENHANCED REVERSE TRANSCRIPTASE POLYMERASE CHAIN ASSAY TO DETECT MN IN PATIENTS WITH RENAL CELL CARCINOMA

(75) Inventors: James M. McKiernan, New York, NY (US); Ihor S. Sawczuk, Tenafly, NJ (US); Ralph Buttyan, New York; Neil H. Bander, Chappaqua, both of NY (US)

(73) Assignees: The Trustees of Columbia University in the City of New York, New York, NY (US); Cornell Research Foundation, Inc., Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/403,145

(22) Filed: Oct. 15, 1999

Related U.S. Application Data

(63) Continuation of application No. PCT/US98/07719, filed on Apr. 15, 1998, which is a continuation-in-part of application No. 08/839,698, filed on Apr. 15, 1997, now Pat. No. 6,087,098.

(51) Int. Cl.[7] .............................. C12Q 1/68; C12P 19/34

(52) U.S. Cl. ........................ 435/6; 435/91.1; 435/91.2

(58) Field of Search ............................ 435/6, 91.2, 91.1

(56) References Cited

U.S. PATENT DOCUMENTS

| 4,935,344 A | 6/1990 | Bander et al. |
| 5,387,676 A | 2/1995 | Zavada et al. |

OTHER PUBLICATIONS

Bander et al. (1989) "Analysis of a Mouse Monoclonal Antibody That Reacts with a Specific Region of the Human Proximal Tubule and Subsets Renal Cell Carcinoma," *Cancer Research* 49:6774–6780.

Brewer et al. (1996) "A Study of Biomarkers in Cervical Carcinoma and Clinical Correlation of the Novel Biomarker MN," *Gynecol. Oncol.* 63(3): 337–344.

Der et al. (1981) "A Tumor–specific Membrane Phosphoprotein Marker in Human Cell Hybrids," *Cell* 26:429–438.

Kranenborg et al. (1995) "Development and Characterization of Anti–Renal Cell Carcinoma X Antichelate Bispecific Monoclonal Antibodies for Two–Phase Targeting of Renal Cell Carcinoma," *Cancer Res.* 55(23):5864s–5867s.

Kusama et al. (1991) "Tumor Markers in Human Renal Cell Carcinoma," *Tumor Biol* 12:189–197.

Liao et al. (1994) "Identification of the MN Antigen as a Diagnostic Biomarker of Cervical Intraepithelial Squamous and Glandular Neoplasia and Cervical Carcinomas," *Am. J. Pathol.* 145 (23):598–609.

McKiernan, J.M. et al., (1997) "Expression of Tumor–associated Gene MN: A potential biomarker for human renal cell carcinoma", *Cancer Research*, 57:2362–2365.

(List continued on next page.)

*Primary Examiner*—W. Gary Jones
*Assistant Examiner*—Jehanne Souaya
(74) *Attorney, Agent, or Firm*—John P. White; Cooper & Dunham LLP

(57) ABSTRACT

This invention provides methods of: (a) diagnosing; (b) determining the stage of; and (c) monitoring the effect of a therapeutic intervention for a renal cell carcinoma in a human subject which comprises detecting the expression of the MN gene. In one embodiment, the method is directed to detection of the renal cell carcinoma known as clear cell carcinoma. In another embodiment, the method is used as a peripheral blood assay. In another embodiment, the method is a polymerase chain reaction assay for amplifying and detecting the presence of the cDNA molecule encoding the MN protein.

6 Claims, 4 Drawing Sheets

OTHER PUBLICATIONS

Olive et al. (1997) "Characterisation of γδT cells in renal cell carcinoma patients by polymerase chain reaction analysis of T cell receptor transcripts," *Cancer Immunology Immunotherapy.* 44:27–34.

Oosterwijk et al. (1993) "Antibody Localization in Human Renal Cell Carcinoma: A Phase I Study of Monoclonal Antibody G250," *J. Clin. Oncol.* 11(4):738–750.

Oosterwijk et al. (1986) "Monoclonal Antibody G 250 Recognizes a Determinant Present in Renal–Cell Carcinoma and Absent from Normal Kidney," *Intl. J. Cancer* 38:489–494.

Oosterwijk et al. (1996) "Molecular Characterization of the Renal Cell Carcinoma–Associated Antigen G250," *Proc. Am. Urol. Assn.* 155, 542A (abstract No. 925).

Oosterwijk et al. (1995) "Radiolabled Monoclonal Antibody G250 in Renal–Cell Carcinoma," *World J. Urol.* 13(3):186–190.

Oosterwijk et al. (1995) "The Use of Monoclonal Antibody G250 in the Therapy of Renal–Cell Carcinoma," *Semin. Oncol.* 22(1):34–41.

Opavský et al. (1996) "Human Mn/ca9 Gene, a Novel Member of the Carbonic Anhydrase Family:Structure and Exon to Protein Domain Relationships," *Genomics* 33:480–487.

Pastorek et al. (1994) "Cloning and Characterization of MN, a Human Tumor–associated Protein with a Domain Homologous to Carbonic Anhydrase and a Putative Helix–loop–helix Dna Binding Segment," *Oncogene* 9:2877–2888.

Pastorekova et al. (1997) "Carbonic Anhydrase IX, MN/CA IX: Analysis of Stomach Complementary DNA Sequence and Expression in Human and Rat Alimentary Tracts," *Gastroenterology* 112(2):398–408.

Steffens et al. (1997) "Targeting of Renal Cell Carcinoma with Iodine–131–Labeled Chimeric Monoclonal Antibody G250," *J. Clin. Oncol.* 15(4):1529–37.

Surfus et al. (1996) "Anti–Renal–Cell Carcinoma Chimeric Antibody G250 Facilitates Antibody–Dependent Cellular Cytotoxicity with In Vitro and In Vivo Interleukin–2–Activated Effectors," *J. Immunother Emphasis Tumor Immunol.* 19(3):184–191.

Uemura et al. (1994) "Immunization with Anti–Idiotype Monoclonal Antibodies Bearing the Internal Image of the Renal–Cell Carcinoma–Associated Antigen G250 Induces Specific Cellular Immune Responses," *Int. J. Cancer* 59(6):802–807.

Uemura et al. (1994) "Internal Image Anti–Idiotype Antibodies Related to Renal–Cell Carcinoma–Associated Antigen G250," *Int. J. Cancer* 56(4): 609–614.

Uemura et al. (1994) "Vaccination with Anti–Idiotype Antibodies Mimicking a Renal Cell Carcinoma–Associated Antigen Induces Tumor Immunity," *Int. J. Cancer* 58(4): 555–561.

Van Dijk et al. (1994) "Therapeutic Effects of Monoclonal Antibody G250, Interferons and Tumor Necrosis Factor, In Mice with Renal–Cell Carcinoma Xenografts," *Int. J. Cancer* 56(2): 262–268.

Zavada et al. (1993) "Expression of MaTu–MN Protein in Human Tumor Cultures and in Clinical Specimens," *Int. J. Cancer* 54(2): 268–274.

G3-PDH ← 451 bp

MN ← 386 bp

G3-PDH ← 451 bp

MN ← 386 bp

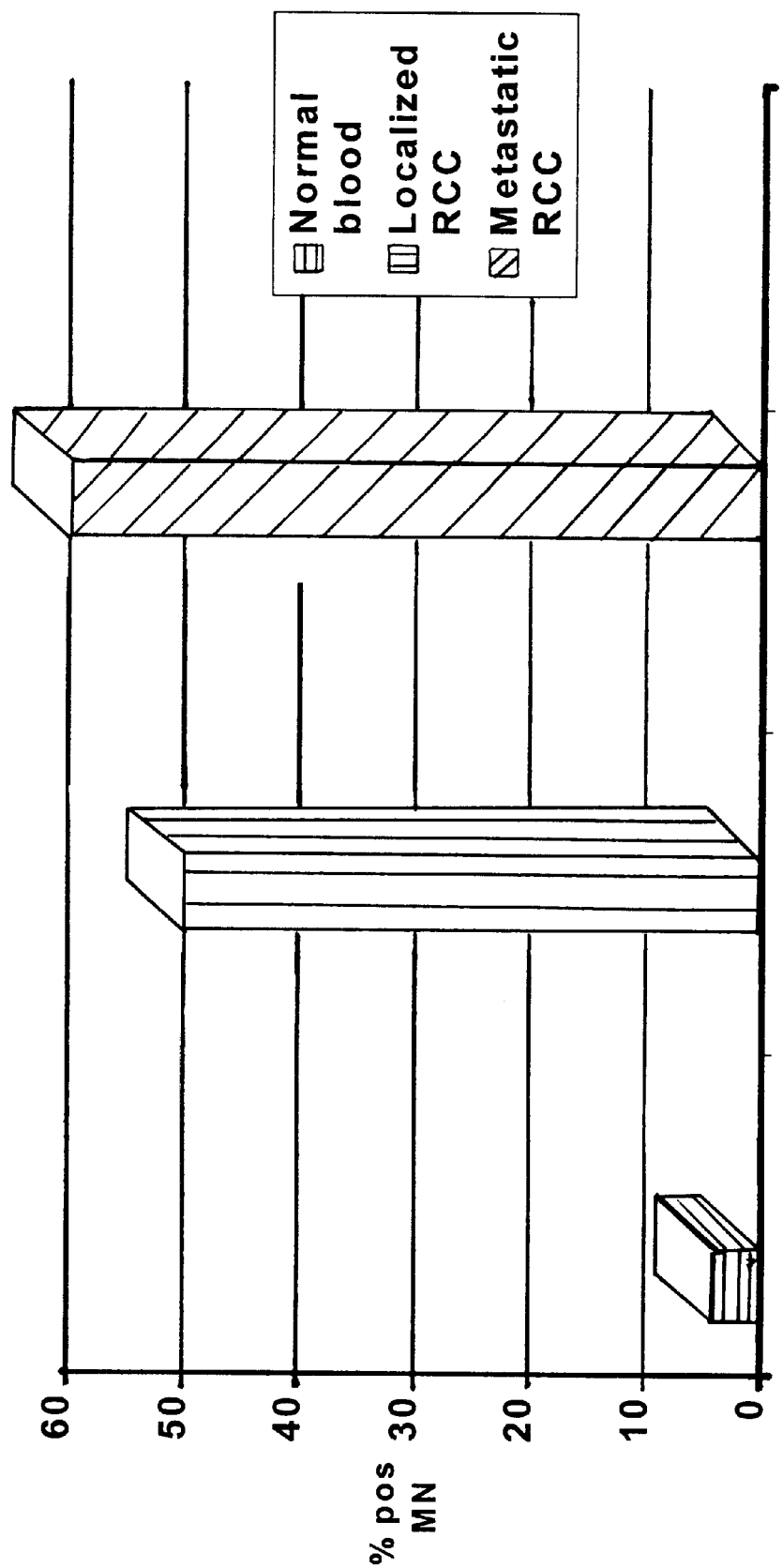

ENHANCED REVERSE TRANSCRIPTASE POLYMERASE CHAIN ASSAY TO DETECT MN IN PATIENTS WITH RENAL CELL CARCINOMA

This application is a continuation of PCT International Application No. PCT/US98/07719, filed Apr. 15, 1998, designating the United States of America, which is a continuation-in-part of and claims priority or U.S. Ser. No. 08/839,698, filed Apr. 15, 1997, now U.S. Pat. No. 6,087,098 the contents of which are incorporated by reference into the present application.

The invention disclosed herein was made with Government support under Grant No. R01 CA70769-01 from the National Institutes of Health. Accordingly, the U.S. Government has certain rights to this invention.

BACKGROUND OF THE INVENTION

Throughout this application, various publications are referenced by arabic numbers in parentheses. Full citations for these publications may be found listed at the end of the specification immediately preceding the Sequence Listing and the claims. The disclosures of these publications in their entireties are hereby incorporated by reference in order to more fully describe the state of the art as known to those skilled therein as of the date of the invention described and claimed herein.

For several forms of solid tumors, the process of tumor detection and staging has been greatly improved by the development of assays that detect and measure tumor-specific markers in specimens of patient tissues or body fluids. As exemplified by the use of prostate specific antigen (PSA) screening for prostate cancer (1), such assays have the potential of revolutionizing the clinical approach to diagnosis, staging and monitoring the effect of therapeutic intervention in human malignancies. Many of these tumor marker assays are based on immunologic detection of the tumor marker protein. Increasingly, tumor detection methods that involve DNA- and RNA-based assays of patient specimens are being used (2,3,4). With the use of polymerase chain reaction (PCR) technology to amplify unique genetic sequences which are markers for malignancy, these assays can now detect small numbers of cancer cells in patient blood specimens (5,6).

With regard to kidney cancer, it is estimated that 28,800 new cases will be diagnosed in 1997, resulting in approximately 11,700 deaths (8). The majority of deaths will be caused by renal cell carcinoma. If renal cell carcinoma tumors are detected while still confined to the kidney, radical nephrectomy results in excellent long term survival. Unfortunately, symptoms of disease rarely occur prior to metastatic spread. Once renal cell carcinoma has metastasized, survival rates are less than 10% at five years (9). Until now, no suitable diagnostic marker existed for renal cell carcinoma detection, staging or for monitoring the effect of therapy.

This invention provides a PCR-based technique to detect the malignant renal cell marker MN in a peripheral blood sample. The MN protein was first detected on the cell surface of the highly-malignant cervical cancer cell line, HeLa (10). MN expression has also been detected in human cervical and ovarian tumor specimens, but not in normal cervical or ovarian tissue. These results suggested that MN might be a useful marker for screening certain gynecological malignancies (11). In these early studies, MN expression was also detected in normal epithelial cells of the gastric mucosa. Its restricted expression in this normal tissue was viewed as unlikely to interfere with tumor-specific detection in tissues outside of the gastrointestinal tract (11,12).

The availability of the complete cDNA sequence for the MN gene product (10) allowed the design of specific PCR primers that amplify a portion of the MN cDNA in a reverse transcriptase-PCR (RT-PCR) assay. The assay is useful for-the diagnosis and molecular staging of renal cell carcinoma. The assay is also useful for the follow-up of renal cell carcinoma therapy. The assay is particularly sensitive for detection of a subset of renal cell carcinoma known as clear cell carcinoma. Quite importantly, the assay is capable of detecting the renal cell carcinoma marker MN in a peripheral blood test.

SUMMARY OF THE INVENTION

This invention provides methods of: (a) diagnosing; (b) determining the stage of; and (c) monitoring the effect of a therapeutic intervention for a renal cell carcinoma in a human subject which comprises detecting the expression of the MN gene. In one embodiment, the method is directed to detection of the renal cell carcinoma known as clear cell carcinoma. In another embodiment, the method is used as a peripheral blood assay. In another embodiment, the method is a polymerase chain reaction assay for amplifying and detecting the presence of the cDNA molecule encoding the MN protein.

BRIEF DESCRIPTION OF THE FIGURES

FIG. 1. MN expression in HeLa cell line and normal human tissue libraries.

FIG. 2. MN expression in renal carcinoma cell lines.

FIG. 3. MN expression in tissue from renal carcinoma patients.

FIG. 4. MN expression in peripheral blood samples from: (a) normal human subjects; (b) patients with localized renal cell carcinoma (RCC) ; and (c) patients with metastatic RCC. In (a), 3 of 28 normal blood samples (10%) were positive for MN (left). In (b), 9 of 18 blood samples (50%) from patients with localized RCC were positive for MN (middle). In (c), 3 of 5 blood samples (606) from patients with metastatic RCC were positive for MN (right). The Y-axis (% pos MN) displays the percentage of peripheral blood samples in each group that tested positive for MN using the enhanced RT-PCR assay (i.e. Southern blot detection of the amplified band).

DETAILED DESCRIPTION OF THE INVENTION

Figure 1A:
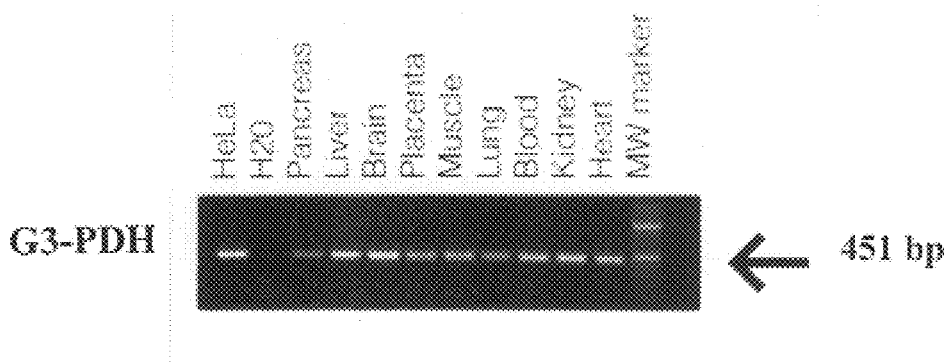
FIG. 1A. Human glucose 3-phosphate dehydrogenase (G3-PDH) primers were utilized in a parallel reaction to amplify a 451 bp G3-PDH fragment to confirm mRNA integrity.

This invention provides a method for diagnosing a clear cell renal carcinoma in a human subject which comprises:

(a) obtaining mRNA from a sample of the subject's peripheral blood; (b) preparing cDNA from the mRNA from step (a); (c) amplifying DNA encoding MN present in the cDNA prepared in step (b); and (d) detecting the presence of any resulting amplified DNA, the presence of such amplified DNA being diagnostic for clear cell renal carcinoma.

In one embodiment, in step (c) amplification of DNA encoding MN is effected by a polymerase chain reaction utilizing at least two oligonucleotide primers. In another embodiment, each of the primers is capable of specifically hybridizing with DNA encoding MN. In another embodiment, the primers comprise oligonucleotides having the sequence 5'-GGGACAAAGAAGGGGATGAC-3' (SEQ ID NO:1) and 5'-AAAGGCGCTGAGGTGAA-3' (SEQ ID NO:2).

In one embodiment, the presence of any amplified DNA in step (d) is detected using a labeled oligonucleotide probe which specifically hybridizes with the amplified DNA. In another embodiment, the labeled probe is radiolabeled with $^{32}P$.

This invention provides a method for determining the stage of a clear cell renal carcinoma in a human subject which comprises: (a) obtaining mRNA from a sample of the subject's peripheral blood; (b) preparing cDNA from the mRNA from step (a); (c) amplifying DNA encoding MN present in the cDNA prepared in step (b); (d) determining the amount of any resulting amplified DNA; and (e) comparing the amount of amplified DNA determined in step (d) with the amount of amplified DNA indicative of each stage of clear cell renal carcinoma so as to thereby determine the stage of the clear cell renal carcinoma in the human subject.

In one embodiment, in step (c) amplification of DNA encoding MN is effected by a polymerase chain reaction utilizing at least two oligonucleotide primers. In another embodiment, each of the primers is capable of specifically hybridizing with DNA encoding MN. In another embodiment, the primers comprise oligonucleotides having the sequence 5'-GGGACAAAGAAGGGGATGAC-3' (SEQ ID NO:1) and 5'-AAAGGCGCTGAGGTGAA-3' (SEQ ID NO:2).

In one embodiment, the presence of any amplified DNA in step (d) is detected using a labeled oligonucleotide probe which specifically hybridizes with the amplified DNA. In another embodiment, the labeled probe is radiolabeled with $^{32}P$.

This invention provides a method for monitoring the progression of a clear cell renal carcinoma in a human subject which comprises: (a) determining the stage of the clear cell renal carcinoma in the human subject at a first time according to the method of claim 7; (b) determining the stage of the clear cell renal carcinoma in the human subject at a subsequent time or times; and (c) comparing the stage determined in (a) with the stage determined in (b) so as to thereby monitor the progression of the clear cell renal carcinoma in the human subject.

This invention provides a method for detecting MN gene expression in a biological sample from human subject which comprises: (a) extracting mRNA from the sample; (b)contacting the mRNA from step (a) with reverse transcriptase under conditions allowing for the production of cDNA; (c) contacting the cDNA produced from step (b) with a pair of polymerase chain reaction oligonucleotide primers capable of specifically hybridizing with DNA encoding MN; (d) contacting the composition resulting from step (c) with DNA polymerase under conditions allowing for the extension of the primers so as to amplify a DNA molecule having the sequence flanked by the primers; and (e) detecting the amplified DNA from step (d), thereby detecting MN expression in the biological sample from the subject.

In one embodiment, the pair of primers in step (c) are 5'-GGG ACA AAG AAG GGG ATG AC-3' (SEQ ID NO:1) and 5'-AAA GGC GCT GAG GTG AA-3' (SEQ ID NO:2). In one embodiment, the biological sample is a peripheral blood sample. In one embodiment, the renal cell carcinoma is clear cell carcinoma. In one embodiment, step (d) is repeated 35 times. In one embodiment, the amplified DNA detected is 386 base pairs long.

In one embodiment, the cDNA molecule encoding a portion of the MN protein is detected by: (a) loading the composition of step (e) onto a gel; (b) electrophoresing the cDNA of the composition into the gel; (c) ethidium bromide staining the cDNA inside the gel; and (d) visualizing the ethidium bromide stained cDNA under ultraviolet light, thereby detecting the cDNA molecule encoding a portion of the MN protein.

In another embodiment, the cDNA molecule encoding a portion of the MN protein is detected by: (a) loading the composition of step (e) onto a gel; (b) electrophoresing the cDNA of the composition into the gel; (c) Southern blotting the cDNA inside the gel to a solid support; (d) hybridizing the blotted cDNA on the solid support with a labeled MN DNA probe; and (e) visualizing the labeled MN DNA probe, thereby detecting the cDNA molecule encoding a portion of the MN protein. In one embodiment, the labeled probe comprises a single-stranded probe 386 nucleotides in length and having a sequence complementary to the amplified cDNA. In one embodiment, the labeled probe is radiolabeled with 32P.

This invention provides a method for the detection of MN gene expression in a biological sample from a human subject which comprises: (a) extracting mRNA from the sample; (b) contacting the mRNA from step (a) with reverse transcriptase under conditions allowing for the production of cDNA; (c) contacting the cDNA from step (b) with a pair of polymerase chain reaction oligonucleotide primers capable of specifically hybridizing with DNA encoding MN; (d) contacting the composition from step (c) with DNA polymerase under conditions allowing for the extension of the primers; and (e) detecting the composition from step (d), thereby detecting MN expression in the biological sample from the subject.

This invention provides a method of diagnosing a renal cell carcinoma in a sample from a human subject which comprises: (a) extracting mRNA molecules from the peripheral blood; (b) amplifying a cDNA molecule encoding the MN protein which comprises: (i) contacting the mRNA molecule extract with a nucleic acid molecule primer capable of specifically hybridizing to a nucleic acid sequence site included within the mRNA encoding the MN protein under conditions allowing the primer to specifically hybridize to the mRNA encoding the MN protein; (ii) contacting the composition produced by (i) with reverse transcriptase under conditions allowing the reverse transcriptase to transcribe a single-stranded cDNA molecule copy of the mRNA molecule encoding the MN protein; (iii) heat denaturing the cDNA and mRNA molecule of the composition produced by step (ii); (iv) contacting the composition produced by step (iii) with a first primer capable of specifically hybridizing to a first unique nucleic acid molecule sequence site located on the cDNA molecule complementary to the mRNA encoding the MN protein under conditions allowing the first primer to specifically hybridize with the first unique nucleic acid molecule sequence site; (v) contacting the composition produced by step (iv) with DNA polymerase under conditions allowing the DNA polymerase to synthesize a double-stranded cDNA molecule encoding the MN protein using the first primer to initiate synthesis and the single-stranded cDNA molecule as a template; (vi) heat denaturing the double-stranded cDNA molecule of the composition produced by step (v); (vii) contacting the composition produced by step (vi) with the first primer and a second nucleic acid molecule primer capable of specifically hybridizing with a second unique nucleic acid sequence site located on the other cDNA strand 3' of the first unique site under conditions allowing the first and second primers to specifically hybridize with the first and second unique sequences, respectively, of the cDNA molecule, encoding the MN protein; (viii) contacting the composition produced by step (vii) with DNA polymerase under conditions allowing the DNA polymerase to synthesize cDNA molecules encoding the MN protein using the first or second primers to initiate synthesis and the heat-denatured cDNA molecule encoding the MN protein as a template; and (ix) repeating steps (vi) through (viii) for a sufficient number of times; and (c) detecting the presence of the cDNA molecule encoding the MN protein, positive detection indicating diagnosis of renal cell carcinoma in the subject.

This invention provides a method of monitoring the effect of a therapeutic intervention on the progression of a renal cell carcinoma in a sample from a human subject which comprises: (a) extracting mRNA molecules from the peripheral blood; (b) amplifying a cDNA molecule encoding the MN protein which comprises: (i) contacting the mRNA molecule extract with a nucleic acid molecule primer capable of specifically hybridizing to a nucleic acid sequence site included within the mRNA encoding the MN protein under conditions allowing the primer to specifically hybridize to the mRNA encoding the MN protein; (ii) contacting the composition produced by (i) with reverse transcriptase under conditions allowing the reverse transcriptase to transcribe a single-stranded cDNA molecule copy of the mRNA molecule encoding the MN protein; (iii) heat denaturing the cDNA and mRNA molecule of the composition produced by step (ii); (iv) contacting the composition produced by step (iii) with a first primer capable of specifically hybridizing to a first unique nucleic acid molecule sequence site located on the cDNA molecule complementary to the mRNA encoding the MN protein under conditions allowing the first primer to specifically hybridize with the first unique nucleic acid molecule sequence site; (v) contacting the composition produced by step (iv) with DNA polymerase under conditions allowing the DNA polymerase to synthesize a double-stranded cDNA molecule encoding the MN protein using the first primer to initiate synthesis and the single-stranded cDNA molecule as a template; (vi) heat denaturing the double-stranded cDNA molecule of the composition produced by step (v); (vii) contacting the composition produced by step (vi) with the first primer and a second nucleic acid molecule primer capable of specifically hybridizing with a second unique nucleic acid sequence site located on the other cDNA strand 3' of the first unique site under conditions allowing the first and second primers to specifically hybridize with the first and second unique sequences, respectively, of the cDNA molecule, encoding the MN protein; (viii) contacting the composition produced by step (vii) with DNA polymerase under conditions allowing the DNA polymerase to synthesize cDNA molecules encoding the MN protein using the first or second primers to initiate synthesis and the heat-denatured cDNA molecule encoding the MN protein as a template; and (ix) repeating steps (vi) through (viii) for a sufficient number of times; and (c) detecting the absence or presence of the cDNA molecule encoding the MN protein, thereby monitoring the effect of a therapeutic intervention on the progression of a renal cell carcinoma.

This invention provides a method of determining the stage of a renal cell carcinoma in a sample from a human subject which comprises: (a) extracting mRNA molecules from the sample; (b) amplifying a cDNA molecule encoding the MN protein which comprises: (i) contacting the mRNA molecule extract with a nucleic acid molecule primer capable of specifically hybridizing to a nucleic acid sequence site included within the mRNA encoding the MN protein under conditions allowing the primer to specifically hybridize to the mRNA encoding the MN protein; (ii) contacting the composition produced by (i) with reverse transcriptase under conditions allowing the reverse transcriptase to transcribe a single-stranded cDNA molecule copy of the mRNA molecule encoding the MN protein; (iii) heat denaturing the cDNA and mRNA molecule of the composition produced by step (ii); (iv) contacting the composition produced by step (iii) with a first primer capable of specifically hybridizing to a first unique nucleic acid molecule sequence site located on the cDNA molecule complementary to the mRNA encoding the MN protein under conditions allowing the first primer to specifically hybridize with the first unique nucleic acid molecule sequence site; (v) contacting the composition produced by step (iv) with DNA polymerase under conditions allowing the DNA polymerase to synthesize a double-stranded cDNA molecule encoding the MN protein using the first primer to initiate synthesis and the single-stranded cDNA molecule as a template; (vi) heat denaturing the double-stranded cDNA molecule of the composition produced by step (v); (vii) contacting the composition produced by step (vi) with the first primer and a second nucleic acid molecule primer capable of specifically hybridizing with a second unique nucleic acid sequence site located on the other cDNA strand 3' of the first unique site under conditions allowing the first and second primers to specifically hybridize with the first and second unique sequences, respectively, of the cDNA molecule, encoding the MN protein; (viii) contacting the composition produced by step (vii) with DNA polymerase under conditions allowing the DNA polymerase to synthesize cDNA molecules encoding the MN protein using the first or second primers to initiate synthesis and the heat-denatured cDNA molecule encoding the MN protein as a template; and (ix) repeating steps (vi) through (viii) for a sufficient number of times; and (c) detecting the relative abundance of the cDNA molecule encoding the MN protein, thereby determining the stage of the renal cell carcinoma.

One of ordinary skill in the art will recognize that repeating steps (vi) through (viii) for a sufficient number of times means a number large enough to allow detection of the amplified cDNA by standard methods. Such number of times, in a PCR reaction sufficient for amplification to detect amplified cDNA by standard methods including ethidium bromide staining or Southern blotting, is typically 30 times. A preferred number of times is often 20 to 40 times. In the present invention, 35 times is most preferred. However, a number of times as low as 15 and as high as 100 or more may also achieve amplification sufficient to detect the cDNA of interest.

In one embodiment, the renal cell carcinoma detected is clear cell carcinoma.

In one embodiment, the therapeutic intervention comprises radical nephrectomy. In another embodiment, the therapeutic intervention comprises any one or more of the following immunotherapies: (a) interleukin-2 therapy; (b) interferon; (c) cellular immune therapy; or (d) monoclonal antibody therapy (e.g. a monoclonal antibody recognizing G250 and a cytotoxic agent conjugated thereto). In another embodiment, the therapeutic intervention comprises chemotherapy or radiation therapy.

In another embodiment, the cDNA molecule encoding a portion of the MN protein is detected by: (a) loading the composition of step (ix) onto a gel; (b) electrophoresing the cDNA into the gel; (c) ethidium bromide staining the cDNA inside the gel; (d) visualizing the ethidium bromide stained cDNA under ultraviolet light, thereby detecting the cDNA molecule encoding a portion of the MN protein.

In another embodiment, the cDNA molecule encoding a portion of the MN protein is detected by: (a) loading the composition of step (ix) onto a gel; (b) electrophoresing the cDNA into the gel; (c) Southern blotting the cDNA inside the gel to a solid support such as a nylon or nitrocellulose membrane; (d) hybridizing the blotted cDNA with a radio-labeled MN DNA probe; and (e) visualizing the radiolabeled MN DNA probe by autoradiography, thereby detecting the cDNA molecule encoding a portion of the MN protein. This method is particularly useful for detection of MN expression in samples, such as human peripheral blood, which may have a low abundance of MN.

In one embodiment, the first primer of the above-described PCR methods comprises a nucleic acid molecule with a nucleotide sequence of 5'-GGG ACA AAG AAG GGG ATG AC-3' (SEQ ID NO:1) and the second primer comprises a nucleic acid molecule with a nucleotide sequence of 5'-AAA GGC GCT GAG GTG AA-3' (SEQ ID NO:2).

In one embodiment, the amplified MN cDNA detected is 386 base pairs long. In another embodiment, the sample is peripheral blood.

In one embodiment, the amplified MN cDNA is detected by ethidium bromide staining. In another embodiment, the amplified MN cDNA is detected by Southern blotting and hybridization to a radiolabeled cDNA probe encoding a 386 nucleotide cDNA fragment. In another embodiment, the radiolabel is $^{32}P$.

This invention is illustrated by examples set forth in the Experimental Details section which follows. This section is provided to aid in an understanding of the invention but is not intended to, and should not be construed to, limit in any way the invention as set forth in the claims which follow thereafter.

EXPERIMENTAL DETAILS EXAMPLE 1

Introduction. MN is a 51 kd transmembrane glycoprotein that is associated with a malignant phenotype in human gynecological tumors. We have performed a preliminary analysis to determine whether MN is expressed in other genitourinary tissues, especially renal cell carcinoma.

Methods. A reverse transcriptase polymerase chain reaction (RT-PCR) assay was designed using oligonucleotide primers specific for the human MN gene. This assay identifies MN gene expression based on amplification of a 386 base pair (bp) DNA fragment from reverse transcribed messenger RNA. This assay was applied to RNAs extracted from: (a) human cell lines; (b) primary human renal tissue and tumors; and (c) peripheral blood specimens.

Results. The RT-PCR assay allowed us to identify the expected 386 bp product when applied to Hela cell RNA (human cervical cancer). The product was cloned and sequenced and confirmed as MN. Normal human kidney, intestine, blood and cultured fibroblasts were negative for MN expression by RT-PCR as was the prostate cancer cell line, LNCaP. In striking contrast, four of five primary renal tumors were positive as well as three human renal cancer cell lines. Of interest, the three positive renal cell lines were also found to stain for the renal tumor marker G250, whereas three additional cell lines that were negative for MN did not stain for G250.

Conclusion. An RT-PCR assay was successfully designed to characterize the expression of the MN gene in genitourinary tissues. Although MN expression was never found in benign tissues, it was frequently found in renal cell carcinoma. Our results suggest that the MN gene is tumor-cell-specific. Therefore, detection of MN expression may be useful in a molecular staging assay for renal cell cancer.

EXAMPLE 2

MN, A Marker for Renal Cell Carcinoma

Summary. MN is a cell surface antigen originally detected in human HeLa cells. Although it is also expressed in normal gastric mucosa, this antigen was previously found to be expressed in cells with a malignant phenotype in certain tissues of the female genital tract (cervix and ovary). Using an oligonucleotide primer set specific for the human nucleotide sequence encoding MN, we performed RT-PCR assays on RNA extracted from human cell lines and tissues to evaluate whether this marker is expressed at sites other than normal gastric mucosa and malignant cervix and ovary. Complementary DNA libraries derived from normal human heart, lung, kidney, prostate, peripheral blood, brain, placenta and muscle were all negative for MN expression. RNA extracted from liver and pancreatic tissue was positive for MN expression. Three of six renal cancer cell lines tested revealed MN expression. In addition, 12 out of 18 samples of human renal cell carcinoma tissue tested positive for MN, all 12 of which were clear cell adenocarcinomas. In conclusion, this survey identified a unique association of MN expression with renal cell cancers, especially those of the clear cell variety, indicating that MN is a useful marker for the diagnosis, staging and therapeutic monitoring of renal cell carcinoma in humans.

Materials and Methods.

Cell Culture. Six human renal carcinoma cell lines SKRC-01, SKRC-08, SKRC-09, SKRC-17, SKRC-39 and SKRC-42 (13), and the human prostate cancer cell line LnCaP, were maintained in RPMI media supplemented with 5% fetal bovine serum, 100 U/ml penicillin and 0.1 mg/ml streptomycin.

Human Tissues. All primary human tissues utilized in this study were obtained through a protocol approved by the institutional review board at Columbia-Presbyterian Medical Center. All patients involved in this study granted informed consent to participate. Approximately 1 gm of fresh normal renal parenchymal tissue and 1 gm of renal cancer was obtained at the time of radical-nephrectomy. In total, 17 specimens containing renal cancer were available and 10 of these specimens had matched tissues obtained from the normal area of the resected kidney. In addition, 1 specimen of normal human kidney was obtained from a patient undergoing radical nephroureterectomy for transitional cell cancer of the renal pelvis. A human prostate was obtained at the time of transurethral resection for bladder outlet obstruction. Tissues were snap-frozen in liquid nitrogen and then stored at −80° C. Frozen sections of each specimen were cut and analyzed to confirm the appropriate presence or absence of renal cell cancer. Human cDNA libraries for normal liver, placenta, pancreas, heart, skeletal muscle, brain, kidney and lung, packaged in λgt11 phage, were obtained from Clontech (Palo Alto, Calif.).

Eight milliliters of peripheral blood was obtained from normal healthy male and female volunteers. Nucleated cells were separated in a ficoll gradient cell separation tube (Vacutainer #362761, Becton-Dickinson, Piscataway, N.J.) as previously described (6). The nucleated cells were then removed from the buffy coat fraction and washed once in phosphate-buffered saline and pelleted. Cell pellets were stored at −80° C. prior to RNA extraction.

RNA Extraction. RNA extraction was performed using a guanidinium thiocyanate-phenol/chloroform technique (14) utilizing the RNazole B reagent of Tel-Test (Friendswood, Tex.). Cells grown in culture were scraped into medium, centrifuged, washed, and directly homogenized (using a Brinkman Tissue Disrupter) with 2 μl RNazole per 20 mm$^2$ of cells growing in a monolayer. Frozen tissues were pulverized under liquid nitrogen and the frozen powder was likewise extracted with RNazole B. The RNA pellet obtained after isopropanol and ethanol precipitation was dried under a vacuum drier and resuspended in 50 μl of RNase-free water. RNA yield was quantified using ultraviolet spectrophotometry at 260 nm. RNA specimens were stored in aliquots at −80°C. prior to reverse transcription.

Reverse Transcription of RNA. One μg of RNA was added to 0.5 μg of oligo dT primer (GIBCO BRL Life Technologies) and brought to a final volume of 20 μl. The samples were placed at 65 ° C. for 5 minutes and then cooled on ice. The downstream or 3' PCR primer (see below) may also be used for priming the reverse transcription of mRNA into cDNA. The primer-RNA mixture was then combined with 200 units of Moloney murine leukemia virus reverse transcriptase (RT) (Superscript II, GIBCO BRL) and 10 units of recombinant RNase inhibitor. The master mixture was completed by adding 1 mM dNTPs, 50 mM Tris-HCl, 75 mM potassium chloride, 3 mM magnesium chloride and 10 mM dithiothreitol according to manufacturer's instructions. The reverse transcription reaction was then carried out at 37° C. for 90 minutes. Samples were stored at −20° C.

Polymerase Chain Reaction Assay for MN Expression. Oligonucleotide primers specific for MN cDNA were designed using the Oligo Software application system. The two primers, 5'-GGG ACA AAG AAG GGGr ATG AC-3' (SEQ ID NO:1) and 5'-AAA GGC GCT GAG GTG AA-3' (SEQ ID NO:2), were chosen so that they would amplify a particular 386 base pair (bp) region of MN cDNA (from position 433 to position 819 of the cDNA sequence). The 5' primer was designed to span the splice junction between the first and second exons within the MN genomic sequence. This design prevents amplification of any product from genomic MN DNA that might contaminate RNA specimens. PCR was performed on the cDNA with a denaturing temperature of 94° C. (1 min), annealing temperature of 57° C. (1 min) and an extension temperature of 72° C. (1 min) for 35 cycles using a Perkin Elmer-Cetus Thermocycler 7,000. As a control for RNA integrity, a separate portion of cDNA was amplified using primers specific for human glucose-3-phosphate dehydrogenase. Positive and negative PCR controls were provided by HeLa cell RNA (strongly positive for MN), which was reverse transcribed to cDNA (to provide a positive control) or not reverse transcribed (to provide a negative control or a control for contamination).

PCR products were then separated by electrophoresis on a 1% agarose gel. DNA fragments were visualized and photographed under UV light subsequent to ethidium bromide staining. The expected band for MN is 386 bp and was identified by co-migration of a DNA marker ladder electrophoresed in an adjacent lane.

Cloning and Sequencing of the MN PCR Product. After amplification using MN primers, the positive 386 bp DNA fragment was excised from the agarose gel (subsequent to RT-PCR assay of HeLa cell RNA) and directly cloned into the TA cloning vector (Invitrogen, San Diego, Calif.) according to the manufacturer's instructions. The cloned 386 bp fragment was sequenced using conventional dideoxy-nucleotide chain termination techniques to confirm identity with the MN transcript.

Enhanced Assay for MN Detection in Human Peripheral Blood by RT-PCR Plus Southern Blot. When enhanced sensitivity of MN detection was desired (e.g., for peripheral blood samples), Southern blotting of PCR-amplified fragments was performed using conventional methods (23). A $^{32}$P-radiolabeled single-stranded 386 base fragment with a nucleotide sequence identical to the cloned 386 bp DNA fragment was then used to detect the amplified, Southern-blotted band using hybridization followed by autoradiography (23).

Many solid supports, including nylon or nitrocellulose membranes, are suitable for the Southern blot DNA transfer. Here, an overnight transfer to a nylon membrane was performed. Following transfer, the membrane was first prehybridized in a stock prehybridization DNA solution and then hybridized at 68° C. for 12 hours in the presence of the $^{32}$P-radiolabeled 386 base single-stranded MN DNA probe. Finally, the membrane was exposed to autoradiographic film for 12 hours to visualize the band.

Results

Detection. Cloning and Sequencing of MN RT-PCR product. Using the oligonucleotide primers that were designed to amplify a 386 bp portion of MN cDNA, we performed an RT-PCR assay on HeLa cell RNA, the first reported source of MN protein. The PCR reaction products were electrophoresed on a 1% agarose gel. Ethidium bromide staining of this gel identified the 386 bp band characteristic of amplification of MN cDNA. The identity of the 386 bp PCR product as a fragment of MN cDNA was confirmed, by cloning and sequencing the amplified DNA fragment. The sequence of this product was identical to the region of the MN cDNA from position 433 to position 819 of the reported cDNA sequence (12), the region that the primers were designed to amplify. A negative control, tested with this RT-PCR assay using non-reverse-transcribed HeLa cell RNA, did not show any amplified products. Likewise, a direct PCR amplification of purified human genomic DNA did not show any amplified products. Based on the designed primers, the genomic DNA-based amplification product exceeds the optimum length for amplification of most PCR-based detection systems.

Figure 1B:
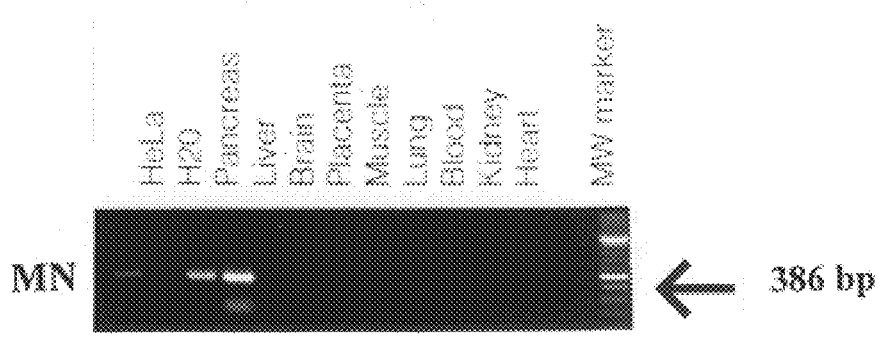
FIG. 1B. The RT-PCR assay detects expression of MN (386 bp) in the HeLa cell line. No MN expression is seen in cDNA libraries from human heart, kidney, lung, muscle, placenta or brain. MN expression is seen in the human pancreas and liver.

MN Expression in Benign Human Tissue. Representative cDNA libraries were obtained from 9 different normal human tissues. These cDNA libraries were directly amplified using the MN primers in a standard PCR reaction. The MN PCR product was not detected in the reaction products from normal human nucleated blood cells, heart, lung, brain, skeletal muscle, placenta or kidney. The 386 bp band characteristic of MN cDNA was detected, however, in the reaction products of human liver and pancreas cDNA libraries (FIG. 1).

Figure 2A:
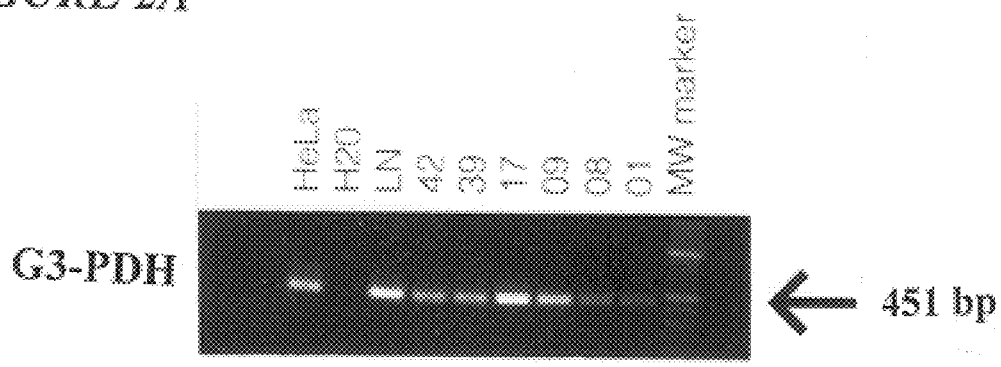
FIG. 2A. G3-PDH controls as in FIG. 1A.
Figure 2B:
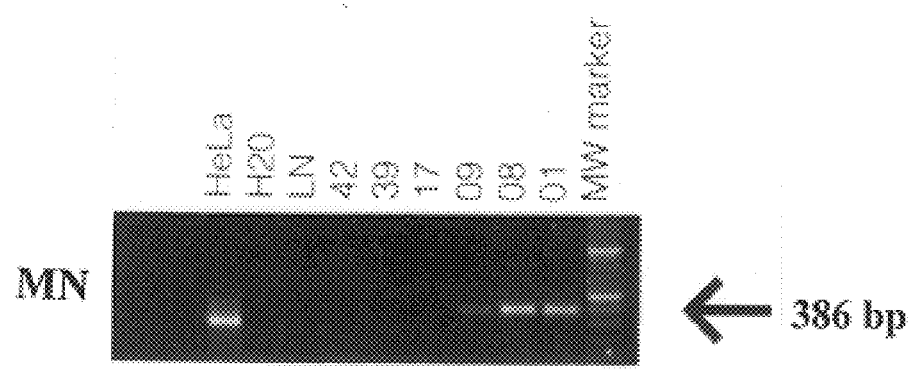
FIG. 2B. The RT-PCR assay detects MN expression in renal carcinoma cell lines SKRC-01, SKRC-08 and SKRC-09. No MN expression is detected in cell lines SKRC-17, SKRC-39 and SKRC-42.

MN Expression in Cultured Human Cells. Total RNA was extracted from human prostate and kidney cancer cell lines grown in culture. While the RNA extracted from the LnCaP cell line (malignant human prostate) showed no expression of the MN transcript, 3 out of 6 human renal carcinoma cell lines revealed strong expression of MN (SKRC-01, SKRC-08 and SKRC-09) (FIG. 2). These three cell lines have previously been shown, by immunohistochemistry, to express the renal cancer cell surface marker known as G250. By contrast, the cell lines that did not express MN are known to be G250-negative (15).

Figure 3A:
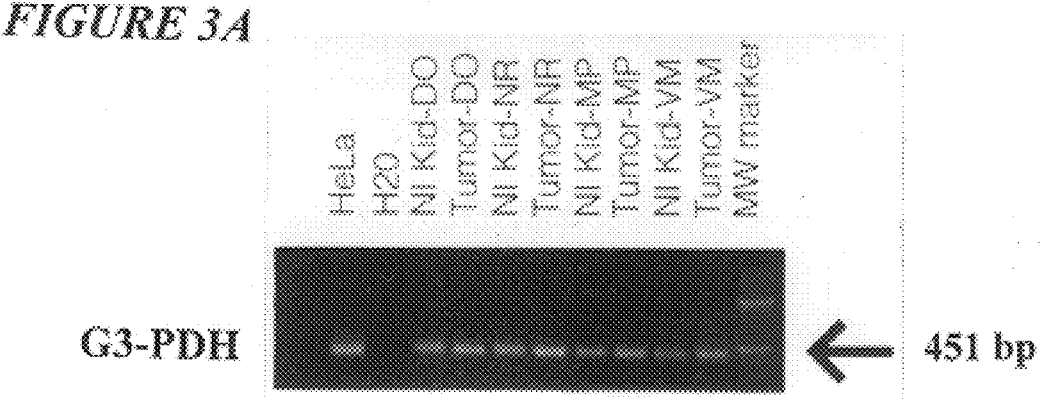
FIG. 3A. G3-PDH controls as in FIG. 1A.
Figure 3B:
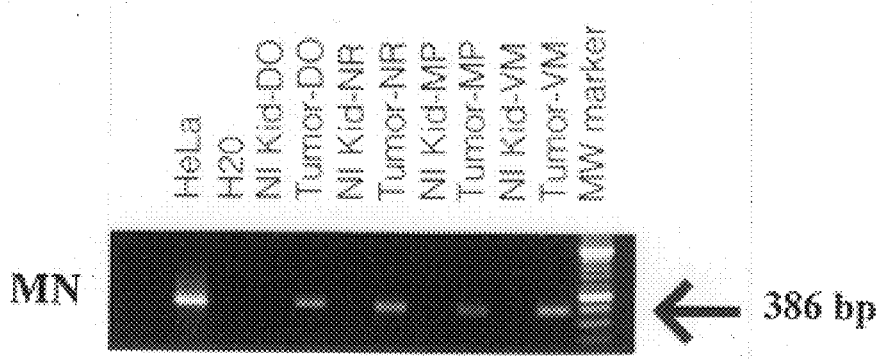
FIG. 3B. The RT-PCR assay detects MN expression in tumor tissue from four renal tumor specimens (patients VM, MP, NR and DO) but does not detect MN expression in normal renal tissue taken from the ipsilateral kidney in the same four patients.

MN Expression in Human Renal Tissue. The finding of MN expression in renal carcinoma cell lines prompted further investigation into MN expression in clinical samples of benign and malignant renal tissue. Normal human renal tissue and primary renal carcinomas were obtained subsequent to radical nephrectomy in renal cancer patients. The RT-PCR analysis of RNAs from these specimens revealed positive MN expression in 12 of 17 renal tumors tested. Histologically, all of the MN-positive specimens were pure clear cell carcinomas (Table 1). For 10 of these 17 renal cancer patients, samples of normal renal tissue were obtained from sites within the ipsilateral kidney and no evidence of MN expression was detected in any of these specimens (FIG. 3).

Discussion

Based on ultrastructural and immunohistochemical evidence, renal cell carcinoma is thought to arise from cells of the proximal tubule (16). Although renal cancer cells share many surface markers with renal tubular cells, no single protein has proven effective as a serum marker in renal cancer. Serum levels of such proteins as erythropoietin and ferritin have been used to follow patients after nephrectomy to detect recurrent disease (17,18,19,20). However, these markers have shown limited clinical usefulness in the diagnosis and staging of renal cancer. Based on the results obtained in this survey of human cell lines, cDNA libraries and tissues, the gene product known as MN is an important marker of certain types of renal cell cancer in humans.

The novel tumor-associated protein known as MN was first isolated from the human cervical cancer cell line HeLa by Der and Stanbridge (10). MN has subsequently been characterized and found to be a 51 kilodalton cell surface protein. The complementary DNA sequence and intron-exon map of the MN coding region have also recently been elucidated (12,21). The MN gene appears to be a member of the carbonic anhydrase family. Its precise role in oncogenesis remains unclear. However, this protein is able to induce a malignant phenotype in cell culture experiments. When MN cDNA was transfected into NIH-3T3 cells, the cells demonstrated loss of cell-cell growth inhibition, failed to grow in monolayers, and acquired a spindle-shaped morphology. In addition, transfection of MN resulted in loss of cellular dependence on growth factors, shorter doubling times, and an increase in DNA synthesis (12). Based on these experiments, Pastorek et al. (12) proposed that the MN protein may play a role in cellular growth regulation.

This survey reports the distribution of expression of the MN gene in several benign and malignant human tissues. The most important results of this survey indicate that the MN mRNA was never detected in samples extracted from normal renal parenchyma (RT-PCR negative in all 10 normal specimens examined). By contrast, in RT-PCR analysis of 17 human renal tumors, 12 were strongly positive for MN expression. All 12 of these MN-positive tumors were found to have a pure clear cell adenocarcinoma histology. Interestingly, MN expression was not observed in granular or papillary tumors of the kidney. The small number of specimens in these latter categories limits statistical inferences. An expanded series of patients with granular and papillary tumors would determine whether MN expression is solely a distinct marker for clear cell adenocarcinoma of the kidney, the most common form of renal cancer.

The expression of the MN messenger RNA in tissue from human liver and pancreas has not been previously described. However, MN is expressed in gastric mucosa of normal subjects and is perhaps localized to tissues of the upper gastrointestinal tract.

The expression of MN detected in 3 human renal tumor cell lines (SKRC-01, SKRC-08 and SKRC-09) is relevant because these cell lines have previously been shown to express a renal cell carcinoma-specific cell surface marker known as G250 (16). The absence of MN expression in SKRC-17, SKRC-39 and SKRC-42 is consistent with this association because these three cell lines have been shown to be G250-negative. The G250 gene has been cloned and sequenced and preliminary analysis indicates homology to, if not identity with, the MN gene (22). The precise relationship between MN gene expression and G250 expression, however, will require further study.

Curative treatment of renal cell carcinoma is available for organ-confined disease and investigation into the immunotherapy of metastatic disease continues. Until now, there was no acceptable renal carcinoma-specific marker available. An effective marker is useful to (a) detect early recurrences, (b) monitor response to immunotherapy regimens, (c) detect extra-renal spread at presentation, or (d) even diagnose renal cancer in cases of complex renal mass. With techniques such as the RT-CPR assay, the clinician may now rely on highly-sensitive techniques to detect microscopic evidence of disease progression. The results described here suggest that MN is a useful marker for renal cell carcinoma, especially clear cell carcinoma.

TABLE 1

| | | | MN expression | |
|---|---|---|---|---|
| Pt | Histology | Grade | Tumor | Normal Kidney |
| 1 | Clear | 2 | pos | neg |
| 2 | Clear | 1 | pos | neg |
| 3 | Clear | 2 | pos | neg |
| 4 | Clear | 2/3 | pos | neg |
| 5 | Clear | 2/3 | pos | neg |
| 6 | Clear | 2 | pos | neg |
| 7 | Clear | 2 | pos | neg |
| 8 | Clear | 1 | pos | neg |
| 9 | Clear | 2 | pos | neg |
| 10 | Clear | 3 | pos | N/A |
| 11 | Clear | 2 | pos | N/A |
| 12 | Clear | 2 | pos | N/A |
| 13 | Gran'r/Pap'y | 1/3 | neg | neg |
| 14 | Granular | 1 | neg | N/A |
| 15 | Granular/Clear | 2 | neg | N/A |
| 16 | Papillary | 2 | neg | N/A |
| 17 | Gran'r/Pap'y | 2/3 | neg | N/A |

Abbreviations used in Table 1. Pt = Patient. Gran'r = Granular. Pap'y = Papillary.

REFERENCES

1. Partin A W and Oesterling J E (1994) The clinical usefulness of prostate specific antigen: update 1994, *J Urol* 152, 1358–1368.
2. Wu A, Ben-Ezra J and Colombero A (1990) Detection of micrometastasis in breast cancer by the polymerase chain reaction, *Lab Invest* 62, 109A.

3. Van Dongen G A, Biakenhoff R M, Van Brink C T, Van Guy F B, de Bree R, Quak J J and Snow G B (1996) Squamous cell carcinoma-associated antigens used in novel strategies for the detection and treatment of minimal residual head and neck cancer, *Anticancer Research* 16, 2409–2413.
4. Stevens G L, Scheer W D and Levine E A (1996) Detection of tyrosinase mRNA from the blood of melanoma patients, *Cancer Epidemiol & Prev* 5, 293–296.
5. Miller W H, Levine K, DeBlasio A, Frankel S R, Dmitrovsky E and Warrell R P Jr (1993) Detection of minimal residual disease in acute promyelocytic leukemia by a reverse transcriptase polymerase chain reaction assay for the PML/RAR-α fusion mRNA, *Blood* 82, 1689.
6. Katz A E, Olsson C A, Raffo A J, Cama C, Perlman H, Seaman E, O'Toole K M, McMahon D, Benson M C and Buttyan R (1994) Molecular staging of prostate cancer with the use of an enhanced reverse transcriptase—PCR assay, *Urology* 43, 765.
7. Anonymous (1995) Detection of epithelial cancer cells in peripheral blood by reverse transcriptase-polymerase chain reaction, *British Journal of Cancer* 71, 278–281.
8. Parker S L, Tong T, Bolden S and Wingo P A (1996) Cancer Statistics 1996, C A 46, 5.
9. Maldazys J D and DeKernion J B (1986) Prognostic factors in metastatic renal cell carcinoma, *J Urol* 136, 376.
10. Der C J and Stanbridge E J (1981) A tumor-specific membrane phosphoprotein marker in human cell hybrids, *Cell* 26, 429.
11. Liao S Y, Brewer C, Zavada J, Pastorek J, Pastorekova S, Manetta A, Berman M, Disaia P J and Stanbridge E J (1994) Identification of the MN antigen as a diagnostic biomarker of cervical intraepithelial squamous and glandular neoplasia and cervical carcinomas, *Am J Pathol* 145, 598.
12. Pastorek J, Pastorekova S. Callebaut I, Mornon J P, Zelnik V, Opavsky R, Zativicova M, Liao S, Portell D, Stanbridge E J, Zavada J, Burny A and Kettmann R (1994) Cloning and characterization of MN, a human tumor-associated protein with a domain homologous to carbonic anhydrase and a putative helix-loop-helix DNA-binding segment, *Oncogene* 9, 2877.
13. Ebert T, Bander N H, Finstad C L, Ramsawak R D and Old L J (1990) Establishment and characterization of human renal cancer and normal kidney cell lines, *Cancer Research* 50, 5531.
14. Chomenzynski P and Sacchi N (1987) Single-step method of RNA isolation by acid guanidinium thiocyanate phenol-chloroform extraction, *Anal Biochem* 162, 156.
15. Oosterwijk E, Ruiter D J, Hoedemaker P J, Pauwels E K, Jonas U, Zwartendijk J and Warnaar SO (1986) Monoclonal antibody G250 recognizes a determinant present in renal cell carcinoma and absent in normal kidney, *Int j Cancer* 38, 489.
16. Bander N H, Finstad C L, Cordon-Cardo C, Ramsawak R D, Vaughan E D Jr, Whitmore W F Jr, Oettgen H F, Melamed M R and Old L J (1989) Analysis of a mouse monoclonal antibody that reacts with a specific region of the human proximal tubule and subsets of renal cell carcinomas, *Cancer Res* 4, 6774.
17. Ljungberg B, Rasmusen T and Glankuist K (1992) Erythropoietin in renal cell carcinoma: evaluation of its usefulness as a tumor marker, *Eur Urology* 21, 160.
18. Partin A W, Criley S R, Steiner M S, Hsieh K, Simons J W, Lumadue J, Carter H B and Marshall F F (1995) Serum ferritin as a clinical marker for renal cell carcinoma: influence of tumor volume, *Urology* 45, 211.
19. Gross A J, Michl V H, Bornhoft G and Diechmann K P (1993) Neuron specific enolase: a serum tumor marker in renal cell carcinoma?, *Eur Urology* 24, 397.
20. Kusama K, Asano M, Moro I, Sekine T, Kazikoe T, Tobisu K and Kishi K (1991) Tumor markers in human renal cell carcinoma, *Tumor Biology* 12, 189.
21. Opavsky R, Pastorekova S, Zelnik V, Gibadulinova A, Stanbridge E J, Zavada J, Kettmann R and Pastorek J (1996) Human MN/CA9 gene, a novel member of the carbonic anhydrase family: structure and exon to protein domain relationships, *Genomics* 33, 480.
22. Oosterwijk E, de Weijert M, von Bokhoven A, Brakenhoff R H, Peelen W P and Debruyne F M J (May 1996) Molecular characterization of the renal cell carcinoma-associated antigen G250, *Journal of Urology* 155, 542A (abstract 925).
23. Sambrook J, Fritsch E F and Maniatis T (1989) *Molecular Cloning: A laboratory manual*, 2d Ed., Cold Spring Harbor Laboratory Press, Salem, Mass.

SECOND SERIES OF EXPERIMENTS

Background of the Invention

Using an enhanced reverse-transcriptase polymerase chain reaction (RT-PCR) assay, we have previously described the expression of the MN/CA9 antigen in renal cell carcinoma (RCC) and its absence in normal renal tissue. The utility of this assay in the detection of circulating renal cancer cells in the peripheral blood was assessed.

As used herein, the designations "MN/CA9" and "MN" are identical and may be used interchangeably. CA is carbonic anhydrase and MN/CA9 designates a gene sequence that is a member of a family of genes.

An enhanced RT-PCR assay using oligonucleotide primers specific for the human MN/CA9 gene was applied to peripheral blood samples in 36 patients with renal tumors including 8 patients with metastatic RCC, 24 patients with localized RCC, 4 patients with benign renal tumors (oncocytoma and angiomyolipoma). 17 males and 15 females with RCC were tested with ages ranging from 37 to 89 and a mean of 62. Blood samples were drawn prior to surgery in patients undergoing nephrectomy. Final pathological stage was T1 in 5 patients, T2 in 7 patients, T3 in 12 patients and metastatic in 8 patients. In addition 56 control patients without evidence of renal masses were tested.

The enhanced RT-PCR assay detected the MN/CA-IX gene product in 3/56 (5%) of normal controls and 0/4 patients with benign renal tumors. Cells expressing the MN/CA9 gene were detected in a total of 14/32 (44%) patients with RCC; 1/5 (20%) T1 patients, 3/7 (43%) T2 patients, 6/12 (50%) T3 patients and 4/8 (50%) of patients with metastatic disease. No correlation was noted between MN/CA9 status and age, sex, tumor grade, histologic subtype, or the presence of microscopic vascular invasion. Pathological stage did correlate with MN/CA9 RT-PCR test results.

The application of this enhanced RT-PCR assay to patients with renal tumors provides a technique which may prove useful in the diagnosis and monitoring of renal cell carcinoma.

An RT-PCR assay to detect renal cancer cells in the peripheral blood was designed and tested. This assay provides a useful adjunct in the detection and management of renal cell carcinoma.

Using a reverse-transcriptase polymerase chain reaction (RT-PCR)assay we previously described the expression of the MN/CA9 gene in renal cell carcinoma (RCC) and its absence in benign renal tissue. In the current study, the utility of an enhanced RT-PCR assay in the detection of renal cancer cells in the peripheral blood is assessed.

Methods

An enhanced MN/CA9 RT-PCR assay was applied to peripheral blood samples from a total of 97 patients. 43 had renal tumors including 5 with benign renal lesions, 29 with localized RCC, and 9 with metastatic RCC. 54 control patients without renal masses were similarly tested. Pathological stage in patients with localized cancer was $T_1N_0M_0$:5, $T_2N_0M_0$:9 and $T_3N_0M_0$:15 patients.

Results

Cells expressing MN/CA9 were detected in 1/54 (1.8%) controls and 18/38 (47%) cancer patients. (p value=0.001). 13/29 (45%) of patients with localized RCC and 5/9 (56%) with metastatic disease tested positive with the assay. No patient with a benign renal mass exhibited MN/CA9 expression. All positive blood test results were noted in patients with clear cell RCC. No correlation was noted between MN/CA9 results and age, sex, tumor grade. A correlation was noted between tumor stage and MN/CA9 results, however this did not reach statistical significance.

The enhanced RT-PCR assay for MN/CA9 provides a highly specific technique to detect circulating renal cancer cells in the peripheral blood which may prove useful in the diagnosis and monitoring of RCC.

THIRD SERIES OF EXPERIMENTS

The incidence of renal cancer has steadily increased over the past 20 years and it is estimated that 29,900 new cases of renal cancer will be diagnosed in 1998, resulting in approximately 12,000 deaths. (1) The majority of these cases are due to RCC. When detected in the early stages, radical nephrectomy can result in durable long-term survival. Unfortunately, symptoms rarely occur before extensive disease is present and no effective screening test is available. Metastatic RCC responds poorly to radiotherapy and chemotherapy, and survival rates for patients with advanced disease are less than 10% at five years (2). Despite the association of certain serum protein elevations with RCC, no accurate tumor marker currently exists for detection, staging, differential diagnosis or monitoring response to treatment in RCC.

The technique of polymerase chain reaction (PCR) amplification was first described in 1986 by Saiki et al. and has subsequently been shown to be powerful and accurate in the detection of small quantities of genetic material isolated from clinical specimens. (3) PCR based detection assays now exist for several tumors including prostate, leukemia, thyroid, melanoma, breast, and colon (4–8). The MN/CA9 gene was first cloned by Pastorek et al. from the malignant cervical cancer cell line, HeLA (9,10).

MN/CA9 expression has also been described in human cervical tumor specimens and benign gastric mucosa. (11) Recently, we described an RT-PCR assay capable of detecting MN/CA9 expression in human tissues and fluids (12). A survey of benign and malignant renal tissues using this RT-PCR assay revealed MN/CA9 expression to be restricted to clear cell carcinoma of the kidney.

This finding was subsequently confirmed by Liao et al. when they described MN/CA9 protein expression in RCC specimens but not in benign renal lesions or fetal kidney tissue. (13)

We have now completed a preliminary analysis of the effectiveness of an enhanced RT-PCR assay for MN/CA9 to detect circulating cells expressing the MN/CA9 gene in the peripheral blood of patients with localized and metastatic renal tumors. These findings suggest that molecular detection of RCC in the peripheral blood is possible, and may prove useful in the diagnosis, monitoring, and staging of renal tumors.

Materials and Methods

Clinical Subjects

In total, 43 blood samples were obtained from patients with renal masses. Age ranged from 37 to 89 with a mean of 62.8, with 28 males and 15 females. (Table 2.) All study subjects donated eight milliliters of peripheral blood. All patients with clinically localized disease were treated with radical nephrectomy. Blood samples were drawn prior to surgery in patients undergoing necphrectomy. Patients with known metastatic disease were tested while enrolled in a trial of autolymphocyte therapy.

Blood samples were tested from 54 control patients without evidence of renal masses. Age ranged from 25 to 79 (mean=47) with 41 males and 13 females. Control patients were either undergoing treatment for some non-renal cancer condition or were healthy volunteers.

TABLE 2

Tumor grade, stage and patient age

| Histology | Classification | Grade | Age |
|---|---|---|---|
| Clear | T1 | 2 | 71 |
| Clear | T1 | 3 | 57 |
| Clear | T1 | 1 | 47 |
| Clear | T1 | 3 | 67 |
| Clear | T1 | 1 | 52 |
| Clear | T2 | 3 | 64 |
| Clear | T2 | 2 | 37 |
| Clear | T2 | 2 | 66 |
| Clear | T2 | 3 | 41 |
| Clear | T2 | 2 | 89 |
| Clear | T2 | 2 | 77 |
| Clear | T2 | 3 | 43 |
| Clear | T2 | 2 | 50 |
| Clear | T3 | 2 | 72 |
| Clear | T3 | 3 | 64 |
| Clear | T3 | 4 | 50 |
| Clear | T3 | 2 | 76 |
| Clear | T3 | 1 | 55 |
| Clear | T3 | 2 | 69 |
| Clear | T3 | 2 | 59 |
| Clear | T3 | 3 | 57 |
| Clear | T3 | 2 | 69 |
| Clear | T3 | 2 | 72 |
| Clear | T3 | 2 | 77 |
| Clear | T3 | 3 | 59 |
| Clear/pap | T3 | 2 | 49 |
| Clear | T3 | 2 | 77 |
| Papillary | T2 | 2 | 64 |
| Clear | $M_1$ | NA | 67 |
| Clear | $M_1$ | NA | 66 |
| Clear | $M_1$ | NA | 56 |
| Clear | $M_1$ | NA | 58 |
| Clear | $M_1$ | NA | 68 |
| Clear | $M_1$ | NA | 83 |
| Clear | $M_1$ | NA | 72 |
| Clear | $M_1$ | NA | 41 |
| Clear | $M_1$ | NA | NA |
| Clear | $M_1$ | NA | 72 |
| Clear | $M_1$ | NA | 51 |
| AML | | | 87 |
| AML | | | 48 |

TABLE 2-continued

Tumor grade, stage and patient age

| Histology | Classification | Grade | Age |
|---|---|---|---|
| Oncocytoma | | | 78 |
| Oncocytoma | | | 74 |
| Oncocytoma | | | 77 |

NA = not available, AML angiomyolipoma
Grade and stage not reported for oncocytoma and AML Tumor specimens When available, 1 gm of renal tumor was obtained at the time of surgery for patients with localized disease. 9 patients with localized disease and all patients with metastatic disease did not have tumor tissue available for MN/CA9 testing. Renal tissues were snap-frozen in liquid nitrogen and then stored at −80° C. All specimens were reviewed by a single pathologist (MAR), grade on a scale of 1 to 4, and classified as clear, chromophobic, chromophilic, papillary, oncocytoma, or angiomyolipoma (AML). Localized tumor stage was assigned according to TNM classification. REF Human tissues utilized in this study were obtained through a protocol approved by the Institutional Review Board at Columbia Presbyterian Medical Center.

All patients involved in this study granted informed consent to participate.

RNA Extraction

Peripheral blood mononuclear cells were purified via a sodium citrate gradient cell separation tube (Vacutainer #362761 Becton-Dickson, Piscataway, N.J.) as previously described. (14) The nucleated cells were then washed once in phosphate buffered saline and pelleted. Cell pellets were stored at −80° C. prior to RNA extraction. RNA extraction was performed using a guanidium thiocyanate phenol and chloroform technique (15) utilizing the RNazole B reagent of Tel-Test (Friendswood, Tex.). Frozen tissues were pulverized under liquid nitrogen and the frozen powder was likewise extracted with RNazole B. The RNA pellet obtained after isopropanol and ethanol precipitation was dried and resuspended in 50 µl of Rnase-free water. RNA specimens were stored in aliquots at −80° C. prior to reverse transcription.

Reverse Transcription of RNA minutes and then cooled on ice. The primer RNA mixture is then combined with 200 units of Moloney murine leukemia virus reverse transcriptase (RT2 Superscript II, GIBCO ERL) and 10 units of cloned Rnase inhibitor. The mixture is completed by adding ImM of dNTP, 50 mM of Tris-HCL, 75 mM potassium chloride, 3 mM of magnesium chloride, and 10 mM dithiothreitol—The reverse transcription reaction is then carried out at 37° C. for 90 minutes. Samples are stored at −20° C.

PCR Assay for MN/CA9

Oligonucleotide primers specific for MN/CA-9 cDNA were designed as previously described. PCR was performed on the cDNAs with a denaturing temperature of 94° (1 min), annealing temperatures of 57° C. (1 min) and an extension temperature of 72° (1 min) for 40 cycles (Perkin Elmer Cetus Thermocycler 7,000). As a control for RNA integrity, a separate portion of cDNA is amplified using primers specific for human glyceraldehyde-3-phosphate dehydrogenase primers. Positive and negative PCR controls are provided by HeLa cell RNA (strongly positive for MN), that is reverse transcribed to cDNA (to provide a positive control) or not reverse transcribed (to provide a negative control). PCR products were then separated by electrophoresis on a 1% agarose gel. DNA fragments were visualized and photographed under UV light with ethidium bromide.

Enhanced Detection of PCR Product: The 386 bp band representing the PCR product derived from HeLa cell mRNA was purified from 1.0% agarose gel and inserted into pCRII cloning vector (Invitrogen). This clone was used as a single stranded DNA probe for Souther blot hybridization. Southern blotting of gel fractionated PCR products derived from peripheral blood mRNA was performed following standard techniques (16). DNA fragments were fixed to a positively charged nylon membrane by ultraviolet light and baking at 80° C. for 30 minutes. The Southern blots were hybridized in the presence of the sequence specific $P^{32}$ labeled MC/CA9 probe for 16 hours at 68° C. Southern blots were rinsed in SDS and SSC buffers and developed at −70° C. for 12 hours.

Statistical Analysis

Pathological and clinical characteristics were correlated with the detection of MN/CA9 in the peripheral blood using chi square analysis and the Mantel-Haenszel chi square test. All statistical analysis was performed using the SAS software package.

Results

The MN/CA9 gene was detected in the peripheral blood in 1/54 (1.8%) of normal controls and 0/5 patients with benign renal lesions. MN/CA9 expression was detected in a total of 18/38 (47%) patients with RCC. The difference in detection rates between the control and cancer patients was statistically significant using chi square analysis (p=0.001).

The specificity of this test was 98% with a sensitivity of 47% in all patients with RCC. Positive predictive value was 95% and negative predictive value was 76%. A total of 13/29 (45%) patients with localized RCC and 5/9 (56%) patients with metastatic disease tested positive for MN/CA9 was detected in 2/5 (40%) $T_1N_0M_0$ patients, 4/9 (44%) $T_2N_0M_0$, 7/15 (47%) $T_3N_0M_0$ patients (Table 3).

TABLE 3

MN detection in the peripheral blood by tumor stage

| Stage | Total | Positive (%) |
|---|---|---|
| $T_1N_0M_0$ | 5 | 2(40) |
| $T_2N_0M_0$ | 9 | 4(44) |
| $T_3N_0M_0$ | 15 | 7(47) |
| Metastatic | 9 | 5(56) |
| Controls | 54 | 1(2) |

No correlation was noted between MN/CA9 status and patient age, sex, or tumor grade. An increasing incidence of positive blood results for MN/CA9 was noted with increasing tumor stage however this trend did not reach statistical significance (p value=0.61). (Table 3)

Twenty six tumor samples were available for testing. (Table 4) There was a significant correlation between tumor histology and MN/CA9 expression in the tumor with 0/5 benign lesions expressing MN/CA9 and 19/21 (95%) clear cell tumors expressing MN/CA9 . (p value=0.001). This correlation was also noted for MN/CA9 blood results with all non-clear cell patients testing negative and 18/37 clear cell patients testing positive, however this correlation did not reach statistical significance using chi-square analysis (p value=0.087). (Table 5).

TABLE 4

MN expression in primary tumor (when available)

| Histology | Total | Positive (%) |
|---|---|---|
| Clear | 21 | 19(91) |
| Oncocytoma | 3 | 0 |
| AML | 2 | 0 |

17 cases without tumor available for testing
(16 clear cells, 1 papillary)

TABLE 5

MN detection in the peripheral blood by tumor histology

| Histology | Total | Positive (%) |
|---|---|---|
| Clear | 37 | 18(49) |
| Oncocytoma | 3 | 0 |
| AML | 2 | 0 |
| Papillary | 1 | 0 |

Discussion

Based on immunohistochemical evidence, RCC shares many cell surface markers with renal tubular cells and is thought to arise from cells of the proximal tubule (17) Unlike adenocarcinoma of the prostate, no single protein has proven useful as a tumor marker in RCC. Serum levels of erythropoietin, ferritin, neuron specific enolase, and transforming growth factor-β have been measured in an effort to monitor patients following nephrectomy or predict prognosis. (18–22). However, these markers have not proven useful in the clinical management of patients with renal tumors.

The tumor-associated antigen MN/CA9 was first described as a cell surface protein on the HeLa cell line. (23). The gene coding for MN/CA9 has been cloned and characterized by Pastorek et al. and appears to be a newly described member of the carbonic anhydrase family. (9) The gene is able to induce a malignant phenotype in cell culture experiments and transfection of MN/CA9 into benign cell lines results in loss of cellular dependence on growth factors, shorter doubling times and an increase in DNA synthesis. (22) We have previously described the detection of MN/CA9 using an RT-PCR assay, in samples of human clear cell carcinoma of the kidney and absence of expression in normal renal parenchyma from tumor bearing kidneys (12). This restriction of expression has been confirmed by Liao et al. using Western blotting techniques. In their series MN/CA9 protein was not detected in fetal kidney, benign renal cystic tissue, oncocytomas, chromophobic tumors or clear cell tumors of non-renal origin. They propose that antibody staining of pathological material for the MN/CA9 protein may provide a means of differentiating clear cell carcinoma of the kidney from tumors of other histologies.

In the current study we describe the first use of this novel renal tumor marker to detect the presence of circulating kidney cancer cells in the peripheral blood. Our data indicate a high specificity of detection with a false positive rate less than 2%. However the sensitivity for all cancer patients was low at 47% and even in patients with metastatic disease sensitivity only reached 56%. Possible reasons for this include inadequate RNA extraction, on-going immunological clearance of tumor cells from the peripheral blood, or differences in the ability of cells to enter and survive in the peripheral circulation. In addition our 9 metastatic patients were enrolled in an ongoing trial of autolymocyte therapy for RCC, and the impact of this regimen on viability or detection of circulating cancer cells cannot be assessed.

Effective serum tumor markers in RCC are lacking. Potential applications include early detection of recurrence, monitoring response to immunotherapy, screening for asymptomatic disease, or diagnosis of RCC in cases of complex renal masses. The enhanced RT-PCR assay for MN/CA9 is highly specific (98%) and therefore a positive result is strongly associated with malignancy. Screening a large asymptomatic population for a relatively uncommon disease may reveal a higher false positive rate. However, if false positive test merely resulted in a renal ultrasound the morbidity would be negligible.

This type of tumor detection system could also prove useful in evaluation of the complex cystic renal mass when considering intervention. Based on the absence of expression in AML and oncocytoma this assay will also be informative when positive in-patients with benign appearing lesions on radiographic imaging studies. Patients with MN/CA9 expression in the peripheral blood prior to surgical intervention for RCC may benefit from surveillance with blood testing for MN/CA9 as part of the routine post operative care. With the increasing application of nephron sparing surgery in RCC, this assay could improve early detection rates for locally recurrent disease.

This preliminary analysis of the MN/CA9 enhanced RT-PCR assay in patients with RCC has shown that the molecular detection of RCC in the peripheral blood is now feasible. Application of this assay in clinical decision making will require evaluation in a larger group of cancer patients and controls.

REFERENCE FOR THE THIRD SERIES OF EXPERIMENTS

1. Landis H S, Murray T, Bolden S, and Wingo, P A. Cancer statistics 1998. CA, 1998; 48:6–10.
2. Maldazys J D, and DeKernion J B. Prognostic factors in metastatic renal cell carcinoma. J Urol 1986; 136: 376-,
3. Saiki R K, Scharf S, and Galoona F. Enzymatic amplification of beta globin genomic sequences and restriction site analysis of diagnosis of sickle cell anemia. Science 1985; 230:1350-.
4. Wu A, Ben-Ezra J, Colombero A. Detection of micrometastasis in breast cancer by the polymerase chain reaction. Lab. Invest 1990; 62:109A.
5. Van Dongen G A, Biakenhoff R M, Van Brink C T, Van Guy F B, de Bree R, Quak J J and Snow G B, Squamous cell carcinoma-associated antigens used in novel strategies for the detection and treatment of minimal residual head and neck cancer. Anticancer research 1996; 16: 2409,
6. Stevens G L, Scheer W D, and Levine E A. Detection of tyrosinase mRNA from the blood of melanoma patients. Cancer Epidem. & Prev. 1996; 5:293,
7. Miller W H, Levine K, DeBlasio A, Frankel S. R, Dmitrovsky E, and Warrell RP Jr. Detection of minimal residual disease in acute promyelocytic leukemia by a reverse transcriptase polymerase chain reaction assay for the PML/RAR-fusion mRNA. Blood 1993; 82:1689-,
8. Burchill S A, Bradbury M F, Pittmann K, Southgate J, Smith B, and Selby P. Detection of epithelial cancer cells in peripheral blood by reverse transcriptase polymerase chain reaction. British Journal of Cancer 1995; 71: 278–81.
9. Pastorek J, Pastorekova S. Callebaut I, Mornon J P, Zelnik V, Opavsky R, et. al. Cloning and characterization of MN, a human tumor-associated protein with a domain homologous to carbonic anhydrase and a putative helix-loop-helix DNA binding segment. Oncogene 1994; 9: 2877-.
10. Opavsky R, Pastorekova. S, Zelnik V, Gibadulinova A, Stanbridge E J, Zavada J, et. al. Human MN/CA9 gene, a novel member of the carbonic anhydrase family: Structure and exon to protein domain relationships. Genomics 1996; 33: 480-.
11. Liao S Y, Brewer C, Zavada J, Pastorek J. Pastorekova S, Manetta A, et. al. Identification of the MN antigen as a diagnostic biomarker of cervical intraepithelial squamous and glandular neoplasia and cervical carcinomas. Am. J. Path. 1994; 145: 598-.
12. McKiernan J M, Buttyan R, Bander N H, Stifelman M D, Katz A E, Chen M W, et. al. Expression of the tumor-associated gene MN: a potential biomarker for human renal cell carcinoma. Cancer Research 1997; 57: 2362–2366.
13. Liao S Y, Aurelio O N, Jan K, Zavada J, and Stanbridge E J. Identification of the MN/CA9 protein as a reliable diagnostic biomarker of clear cell carcinoma of the kidney. Cancer Research 1997 57: 2827-.
14. Katz A E, Olsson C A, Raffo A J, Cama C, Perlman H, Seaman E, et. al. Molecular staging of prostate cancer with the use of an enhanced reverse transcriptase—PCR assay. Urology 1994, 43: 765-.
15. Chomenzynski P, and Sacchi N. Single-step method of RNA isolation by acid guanidinium thiocyanate-phenol-chloroform extraction. Anal. Biochem. 1987; 162: 156-.
16. Sambrook J, Fritsch E F, and Maniatis T. Molecular Cloning: A Laboratory Manual, 2nd ed. Cold Spring Harbor, New York: Cold Springs Harbor Press 1989: 810.
17. Bander N H, Finstad C L, Cordon-Cardo C, Ramsawak R D, Vaughan E D Jr., Whitmore W F Jr., et. al. Analysis of a mouse monoclonal antibody that reacts with a specific region of the human proximal tubule and subsets renal cell carcinomas. Cancer Research 1989; 4: 6774-.
18. Ljungberg B, Rasmusen T, and Glankuist K, Erythropoietin in renal cell carcinoma: evaluation of its usefulness as a tumor marker. European Urology 1992; 21:160-.
19. Partin A W, Criley S P, Steiner M S, Hsieh K, Simons J W, Lumadue J, et. al. Serumferritin as a clinical marker for renal cell carcinoma: influence of tumor volume. Urology 1995; 45: 211
20. Gross A J, Michl V H, Bornhoft G, and Diechmann K P. Neuron specific enolase: a serum tumor marker in renal cell carcinoma? European Urology 1993; 24: 397,
21. Kusama K, Asano M, Moro I, Sekine T, Kazikoe, T, Tobisu K et. al. Tumor markers in human renal cell carcinoma. Tumor Biology 1991; 12: 189-.
22 Junker U, Knoefel B, Nuske K, Rebstock K, Steiner T., Wunderlich H, et. al. Transforming growth factor beta-1 is significantly elevated in plasma of patients suffering from renal cell carcinoma. Cytokine 1996 8: 794-.
23. Pastorekova S, Zavadova Z, Kostal M, Babusikova 0-Zavada J. A novel quasi viral agent MaTu, is a two-component system. Virology 1992; 187: 620,
24. Zavada J, Zavadova Z, Machon O, Kutinova L, Nemeckova S, Opavsky R, et. al. Transient transformation of mammalian cells by MN protein, a tumor-associated cell adhesion molecule with carbonic anhydrase activity. Int J of Oncology 1997; 10: 857-.

What is claimed is:

1. A method for diagnosing a clear cell renal carcinoma in a human subject which comprises:
   (a) obtaining mRNA from a sample of the subject's peripheral blood;
   (b) preparing cDNA from the mRNA from step (a);
   (c) amplifying cDNA encoding MN prepared in step (b); and
   (d) determining the amount of amplified cDNA from step (c), such amount of amplified DNA being diagnostic for clear cell renal carcinoma.

2. The method of claim 1, wherein in step (c) amplification of DNA encoding MN is effected by a polymerase chain reaction utilizing at least two oligonucleotide primers.

3. The method of claim 2, wherein each of the primers is capable of specifically hybridizing with DNA encoding MN.

4. The method of claim 3, wherein the primers comprise oligonucleotides having the sequence 5'-GGGACAAAGAAGGGGATGAC-3' (SEQ ID NO:1) and 5'-AAAGGCGCTGAGGTGAA-3' (SEQ ID NO:2).

5. The method of claim 1, wherein the presence of any amplified DNA in step (d) is detected using a labeled oligonucleotide probe which specifically hybridizes with the amplified DNA.

6. The method of claim 5, wherein the labeled probe is radiolabeled with $^{32}$P.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (iii) HYPOTHETICAL: N (iv) ANTI-SENSE: N (xi) SEQUENCE DESCRIPTION: SEQ ID NO: 1:

GGGACAAAGA AGGGGATGAC                    20

(2) INFORMATION FOR SEQ ID NO: 2:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: DNA (iii) HYPOTHETICAL: N -continued (iv) ANTI-SENSE: N (xi) SEQUENCE DESCRIPTION: SEQ ID NO: 2:

AAAGGCGCTG AGGTGAA    17